(12) United States Patent
Willuweit et al.

(10) Patent No.: US 10,126,241 B2
(45) Date of Patent: Nov. 13, 2018

(54) MEASURING APPARATUS, MEASURING AND EVALUATION APPARATUS AND MEASUREMENT DATA SYSTEM

(71) Applicant: IFE Innovative Forschungs- und Entwicklungs-GmbH & Co., KG, Harrislee (DE)

(72) Inventors: Thomas Willuweit, Hof (DE); Ralf Griesbach, Hof (DE)

(73) Assignee: IFE Innovative Forschungs- und Entwicklungs GmbH & Co. KG, Harrislee (DE)

( * ) Notice: Subject to any disclaimer, the term of this patent is extended or adjusted under 35 U.S.C. 154(b) by 111 days.

(21) Appl. No.: 15/029,323

(22) PCT Filed: Oct. 14, 2014

(86) PCT No.: PCT/EP2014/072034
§ 371 (c)(1),
(2) Date: Apr. 14, 2016

(87) PCT Pub. No.: WO2015/055663
PCT Pub. Date: Apr. 23, 2015

(65) Prior Publication Data
US 2016/0299075 A1    Oct. 13, 2016

(30) Foreign Application Priority Data

Oct. 14, 2013  (EP) .................................... 13188557

(51) Int. Cl.
  *G01J 1/58*   (2006.01)
  *G01N 21/64*  (2006.01)
  *G01N 21/01*  (2006.01)

(52) U.S. Cl.
  CPC ....... *G01N 21/645* (2013.01); *G01N 21/6402* (2013.01); *G01N 2021/0118* (2013.01);
  (Continued)

(58) Field of Classification Search
  CPC .................... G01N 21/645; G01N 21/6402
  (Continued)

(56) References Cited

U.S. PATENT DOCUMENTS 5,754,294 A    5/1998  Jones et al.
6,044,329 A    3/2000  Kidd
(Continued)

FOREIGN PATENT DOCUMENTS

DE    28 38 498 C2    9/1919
DE    84 07 054 U1    6/1984
(Continued)

OTHER PUBLICATIONS

"Mini Spectrometer USB," UV-Design Product Notes, pp. 1-3; http://www.uv-design.de/spectro.pdf (Sep. 1, 2006).
(Continued)

*Primary Examiner* — David Porta
*Assistant Examiner* — Meenakshi Sahu
(74) *Attorney, Agent, or Firm* — Jenkins, Wilson, Taylor & Hunt, P.A.

(57) ABSTRACT

The present invention provides a measuring apparatus (100) designed to analyze a fluid sample (3) or a luminescent sample (52), wherein the measuring apparatus (100) comprises a radiation receiver device (6, 56) for receiving a light beam guided along a measurement path through the fluid sample or radiation emitted by the luminescent sample (52), and wherein the measuring apparatus comprises at least one connection device (36) for connecting an external electronic device (37) for transferring the measurement signals of the radiation receiver device (6, 56) to an evaluation device (109) of the external electronic device (37) for evaluating the measurement signals.

27 Claims, 6 Drawing Sheets

(52) U.S. Cl.
CPC ............... *G01N 2201/062* (2013.01); *G01N 2201/06113* (2013.01)

(58) Field of Classification Search
USPC .................................................. 250/458.1
See application file for complete search history.

(56) References Cited

U.S. PATENT DOCUMENTS

| | | | |
|---|---|---|---|
| 6,526,298 | B1 | 2/2003 | Khalil et al. |
| 7,358,476 | B2 | 4/2008 | Kiesel et al. |
| 7,369,239 | B2 | 5/2008 | Nagashima et al. |
| 7,491,366 | B2 | 2/2009 | Tokhtuev et al. |
| 7,940,388 | B2 | 5/2011 | Bungo |
| 8,582,103 | B2 | 11/2013 | Willuweit et al. |
| 2003/0058450 | A1 | 3/2003 | Mosley et al. |
| 2005/0229698 | A1 | 10/2005 | Beecroft et al. |
| 2005/0254053 | A1 | 11/2005 | Wright |
| 2005/0254054 | A1 | 11/2005 | Janni |
| 2008/0067328 | A1 | 3/2008 | Fujita |
| 2009/0195776 | A1 | 8/2009 | Durst et al. |
| 2010/0208256 | A1 | 8/2010 | Tang et al. |
| 2010/0214556 | A1 | 8/2010 | Mannhardt et al. |
| 2012/0140227 | A1* | 6/2012 | Willuweit ............... G01J 3/02 356/413 |
| 2016/0305880 | A1 | 10/2016 | Willuweit et al. |

FOREIGN PATENT DOCUMENTS

| | | |
|---|---|---|
| DE | 93 19 749 U1 | 2/1994 |
| DE | 10 2006 004 916 | 8/2007 |
| DE | 10 2009 025 261 | 1/2011 |
| EP | 1 489 403 | 12/2004 |
| EP | 1 792 653 | 6/2007 |
| WO | WO02/060320 A1 | 8/2002 |
| WO | WO 2004/106872 A1 | 12/2004 |
| WO | WO2007/088047 | 8/2007 |
| WO | WO2008/124542 | 10/2008 |
| WO | WO2010/146110 A1 | 12/2010 |
| WO | WO 2015/055627 A2 | 4/2015 |
| WO | WO 2015/055663 A1 | 4/2015 |
| WO | WO 2015/055627 A3 | 7/2015 |

OTHER PUBLICATIONS

"Photodiode", Wikipedia, pp. 1-5 (Sep. 27, 2013).
"Probenehmer 14 Stationaere und Portable Probenemer," Internet Citation. <http://www.hach-lange.de/common/documents/1005/1009/10544_Ebook_D_HL_Katalog_Teil4.pdf> pp. 108-109 (Jan. 1, 2004).
Abstract of Chilean Patent Application No. 1790-1996.
Certificate of Grant corresponding to South African Patent Application No. 2011/09044 dated Aug. 29, 2012.
Decision to Grant corresponding to Mexican Patent Application No. MX/2013/038492 dated Jun. 5, 2013.
Examination Report corresponding to Chilean Patent Application No. 3153-2011 dated Apr. 13, 2013.
International Search Report corresponding to International Patent Application No. PCT/EP2010/058533 dated Oct. 12, 2010.
International Search Report corresponding to International Patent Application No. PCT/EP2014/072034 dated Feb. 17, 2015.
International Search Report corresponding to International Patent Application No. PCT/EP2014/071977 dated Jun. 10, 2015.
Notification Concerning Transmittal of International Preliminary Report on Patentability (Chapter I of the Patent Cooperation Treaty) corresponding to International Patent Application No. PCT/EP2010/058533 dated Jan. 5, 2012.
Notification Concerning Transmittal of International Preliminary Report on Patentability (Chapter 1 of the Patent Cooperation Treaty) corresponding to International Patent Application No. PCT/EP2014/071977 dated Apr. 19, 2016.
Notification Concerning Transmittal of International Preliminary Report on Patentability (Chapter I of the Patent Cooperation Treaty) corresponding to International Patent Application No. PCT/EP2014/072034 dated Apr. 19, 2016.
Notification of Acceptance of South Africa Patent Application No. 2011/09044 dated Jun. 8, 2012.
Notice of Allowance corresponding to U.S. Appl. No. 13/375,396 dated Jul. 31, 2013.
Official Action corresponding to Chinese Patent Application No. 201080027051.3 dated Feb. 18, 2013.
Official Action corresponding to Columbian Patent Application No. 11-171561-4 dated May 9, 2013.
Official Action corresponding to New Zealand Patent Application No. 596659 dated Oct. 25, 2012.
Official Action corresponding to U.S. Appl. No. 13/375,396 dated Nov. 26, 2012.
Written Opinion corresponding to International Patent Application No. PCT/EP2010/058533 dated Dec. 17, 2011.
Written Opinion corresponding to International Patent Application No. PCT/EP2014/71977 dated Mar. 3, 2016.
Written Opinion corresponding to International Patent Application No. PCT/EP2014/072034 dated Mar. 3, 2016.
Office Action corresponding to U.S. Appl. No. 15/651,695 dated Dec. 15, 2017.
Offical Action correspoding to U.S. Appl. No. 15/029,289 dated Jan. 17, 2017.

* cited by examiner

MEASURING APPARATUS, MEASURING AND EVALUATION APPARATUS AND MEASUREMENT DATA SYSTEM

The present invention relates to a measuring apparatus designed to analyze a fluid sample or a luminescent sample. Furthermore, the present invention relates to a measuring and evaluation apparatus comprising such a measuring apparatus and an electronic device for evaluating the measurement data of the measuring apparatus. Moreover, the present invention relates to a measurement data system comprising at least one measuring and evaluation apparatus and a second electronic device for evaluating and/or storing the information of the respective measuring and evaluation apparatus.

Hitherto, spectrometers have been known as measuring apparatus for measuring, evaluating and indicating the concentration of at least one analyte in a fluid sample. The measuring method underlying spectrometers is based on the known physical phenomenon that a light beam experiences an attenuation (extinction) when it passes through a fluid. The attenuation is proportional to the concentration of the analyte and to the measurement path in the fluid through which the light beam has to pass. This physical relationship is described by the Lambert-Beer extinction law. The spectrometer evaluates its measurement results for determining the concentration of the analyte in the fluid sample and displays the result of the evaluation on its display. However, this has the disadvantage that such a measuring apparatus is too large and unwieldy to be portable and to be used for example for measurements on site.

It is an object of the present invention to provide an improved measuring apparatus which allows a more compact design.

This object is achieved by means of a measuring apparatus as claimed in patent claim 1, a measuring and evaluation apparatus as claimed in patent claim 22 and a measurement data system as claimed in patent claim 27.

Accordingly, a measuring apparatus is provided which is designed to analyze a fluid sample or a luminescent sample, wherein the measuring apparatus comprises a radiation receiver device for receiving a light beam guided along a measurement path through the fluid sample or radiation emitted by the luminescent sample, and wherein the measuring apparatus comprises at least one connection device for connecting an external electronic device for transferring the measurement signals of the radiation receiver device to an evaluation device of the external electronic device for evaluating the measurement signals.

The concept underlying the present invention consists in separating the measurement of a fluid sample or a luminescent sample and the evaluation of the measurement results of the fluid sample or of the fluorescent sample, in order thereby to construct the measuring apparatus more compactly, which is advantageous particularly in the case of a portable measuring apparatus. For this purpose, the evaluation of the measurement results of a fluid sample or luminescent sample is not carried out in the measuring apparatus itself, but rather in an external electronic device connectable to the measuring apparatus. Only the measurement of the fluid sample or of the luminescent sample is carried out by the measuring apparatus.

Advantageous configurations and developments of the present invention are evident from the dependent claims.

The invention is explained in greater detail below on the basis of exemplary embodiments with reference to the accompanying figures of the drawing.

In the figures:

In the figures, identical reference numerals designate identical or functionally identical components, unless indicated otherwise.

FIG. 1 illustrates one embodiment of a spectrometer 1 according to the invention as measuring apparatus 100.

The spectrometer 1 serves to analyze a fluid sample 3. In this case, for example, the concentration of at least one analyte in the fluid sample 3 is measured by means of the spectrometer 1.

In this case, the fluid sample 3 may be a liquid, a gas or a liquid mist. Likewise, solid particles may also additionally be contained in a liquid fluid sample or a gaseous fluid sample, such as smoke, for example.

The spectrometer 1 is designed as measuring apparatus 100 in such a way that it can measure clear fluid samples. Furthermore, the spectrometer 1 as measuring apparatus 100 may optionally additionally be designed in such a way that it can measure turbid fluid samples, provided that the spectrometer for a measurement can penetrate through these fluid samples sufficiently with light of a light source of a light source device or illumination device 4 of the spectrometer 1. Turbid fluid samples which can be measured by means of the spectrometer 1 are for example thin suspensions of solids in fluids. These include for example turbid sample waters, pore waters, landfill waters, waste waters, suspensions of ground samples and fertilizers. Furthermore, for example bodily fluids, such as e.g. serum, urine, etc., can also be measured by means of the spectrometer 1.

The spectrometer 1 can be used e.g. for determining the concentration of dissolved water constituents. The water sample may originate for example from an aquarium, garden pond or swimming pool, etc. There are no restrictions with regard to the origin of the water.

Examples of water constituents determinable by the spectrometer 1 are oxygen, ozone, chlorine (free chlorine, total chlorine), nitrogen compounds (total nitrogen), potassium, iron, zinc, heavy metals, ammonium, cyanuric acid, cyanide, urea, carbonate (water hardness), hydrogen peroxide, chloride, nitrite, nitrate or phosphate. In particular, the pH of a fluid sample, e.g. of a water sample, can also be determined by a spectrometer. For this purpose, said sample is admixed with e.g. a one-component indicator, such as phenol red, or with a two-component mixed indicator, for example bromothymol blue/thymol blue, which is then measured photometrically. The indicator used may in this case be identified preferably automatically by the spectrometer 1.

Figure 1:
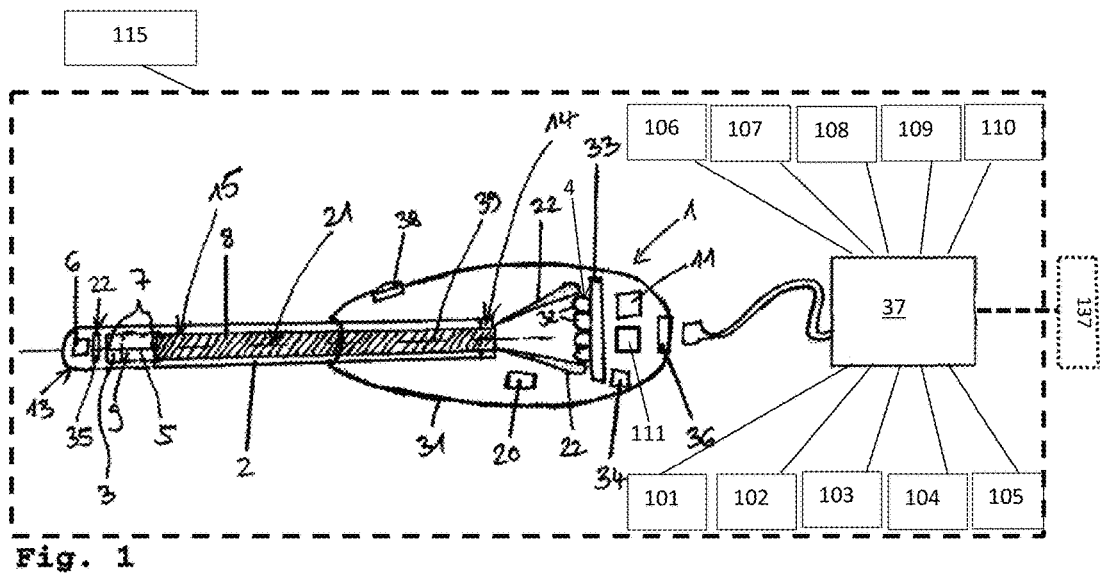
FIG. 1 shows a plan view of a spectrometer as measuring apparatus in accordance with one embodiment of the invention in a partly transparent and partly sectional illustration.

The spectrometer 1 in accordance with one embodiment of the invention as shown in FIG. 1 comprises a housing 31 with a light source device or illumination device 4 for generating at least one light beam 5. Said at least one light beam 5 is guided through a fluid sample 3 received in the spectrometer 1. In this case, the light source device or illumination device 4 may comprise at least one LED 32 or, as illustrated in FIG. 1, an LED array 33 comprising a plurality of LEDs 32 as light source, as is shown in subsequent FIG. 5. By way of example, laser LEDs may be provided as LEDs 32. However, the invention is not restricted to LEDs 32 and in particular laser LEDs. Any other light source may be provided which is suitable for measuring a fluid sample by means of the spectrometer 1 as measuring apparatus 100.

As is shown in the exemplary embodiment in FIG. 1, optionally additionally provision may be made of at least one or more optical devices 22 for collecting and/or guiding the light generated by the LED array 33 into an optical beam path 21 of the spectrometer 1. Such optical devices 22 are for example lenses, mirrors or prisms, etc.

The spectrometer 1 furthermore comprises a sample receptacle device 2 having a sample receptacle 9 for a fluid sample 3. Furthermore, the sample receptacle device 2 comprises a light receiver or radiation receiver device, for receiving the light beam 5 which is generated in the light source device or illumination device 4 of the spectrometer 1 and passes through the fluid sample 3 received in the sample receptacle device 9 along a measurement path 7. By way of example, a photosensor 6 comprising at least one photodiode is used as light receiver or radiation receiver device. Instead of a photosensor 6, any other light receiver can be used which is suitable for receiving light of the light source device or illumination device 4 of the spectrometer 1.

The photosensor 6 as radiation receiver device receives the impinging light beam 5 and converts it into electrical signals which can be evaluated for analyzing or examining the fluid sample 3. The electrical signals depend in each case for example on the impinging light power and/or wavelength of the light beam 5.

In the case of the embodiment of the spectrometer 1 according to the invention as measuring apparatus 100 as shown in FIG. 1, an analog/digital converter 20 is optionally provided, for converting an analog signal of the light receiver or photosensor 6 in FIG. 1 into a digital signal, or vice versa, for transfer to an external electronic device 37, such as e.g. a PC, a smartphone, a tablet PC, a server, etc., which evaluates the signals of the light receiver or photosensor 6. For this purpose, the electronic device 37 comprises e.g. a corresponding evaluation device 109. The result of the evaluation can be displayed by means of a corresponding display of the electronic device 37, e.g. a display of the smartphone or a screen of the PC, a display of the tablet PC, a display or screen connected to the server as display device 110, etc. As a result, for example, the established concentration of an analyte of the fluid sample 3 can be displayed by the display device 110 of the external electronic device.

The external electronic device 37 together with the measuring apparatus 100 forms a measuring and evaluation apparatus 115. This applies to all embodiments of the invention which are described by way of example with reference to FIG. 1 and subsequent FIGS. 2-9.

Furthermore, the external electronic device 37, such as a smartphone, a server, a PC or a tablet PC, etc., may comprise, in addition or as an alternative to the evaluation device 109 and/or the display device 110, a GPS device 101, a time measuring device 102, a camera device 103, a storage device 104, a transmitting device 105, a receiver device 106, a scanner device 107 and/or a microphone device 108, which can be used together with the measuring apparatus 100.

The data of the GPS device 101 can be used for example to determine the position of a measurement performed by the measuring apparatus 100. As a result, the exact geographical position can be assigned to a measurement. In this way, it is possible to verify very simply whether for example a measurement was carried out at the correct location. Moreover, errors in the position determination by a user of the measuring apparatus 100 are avoided.

The time of day and/or the duration of a measurement performed by the measuring apparatus 100, etc., can be determined by the time measuring device 102. As a result, it is possible to verify for example whether the measurement time was complied with and the measurement was carried out correctly by a user of the measuring apparatus 100.

Furthermore, by means of the camera device 103, a user can for example record in the image the location at which said user performed a measurement by the measuring apparatus 100, can photograph a batch number of the measurement sample or of the detection reagent, etc., to mention just a few examples.

Likewise, by means of the scanner device 107 e.g. of a smartphone or tablet PC, a code, e.g. a bar code, a 2D code, etc., can be scanned in, for example a 2D code of a detection reagent used for the measurement by the measuring apparatus 100, etc. It is thereby possible for example to check whether the shelf life of the detection reagent was complied with, what detection reagent was used, etc.

By means of the microphone device 108, it is possible for example to instruct a user of the measuring apparatus 100 how said user has to operate the measuring apparatus 100 and/or the user can dictate additional comments or information or a logging of the measurement into the external measuring device 100 by means of the microphone device 108.

The data of the GPS device 101, of the time measuring device 102, of the camera device 103, of the scanner device 107 and/or of the microphone device 108 can be allocated or assigned to the measurement data obtained by the measuring apparatus 100. The at least one portion or all of the data or signals can be stored in the storage device 104 of the external device 37, e.g. of a smartphone or tablet PC, etc., can be evaluated in the evaluation device 109 of the external electronic device 37, can be displayed on the display device 110, e.g. a screen or display, of the external electronic device 37, and/or can be transferred to a further external device 137, as is indicated by a dotted line in FIG. 1, for example a server, by means of the transmitting device 105 wirelessly and/or in a wired fashion. Likewise, the external electronic device 37, by means of the transmitting device 105, can also transfer data or signals, in particular commands, to the measuring apparatus 100 by means of its transmitting device 105 wirelessly and/or in a wired fashion. This applies to all embodiments of the invention in accordance with FIGS. 1-9.

Furthermore, the external electronic device 37, e.g. the smartphone or the tablet PC, can receive data or signals, in particular commands, etc., via the further external device 137, e.g. a server. By way of example, the external electronic device 37 can control the measuring apparatus 100 by open-loop and/or closed-loop control via the further external device 137. The external electronic device 37 comprises the receiver device 105 for wireless and/or wired reception of data or signals, e.g. commands, etc., of the measuring apparatus 100 and of the further external electronic device 137. This applies to all embodiments of the invention in accordance with FIGS. 1-9.

Optionally, the spectrometer 1 as measuring apparatus 100 may itself comprise at least one dedicated storage device 111 for storing or buffer-storing for example the measurement data or measurement signals, etc. In this case, the storage device 111 can be accessed by the external electronic device 37.

The spectrometer 1 with its sample receptacle device 2 and the photosensor 6 forms a measurement path 7 in the beam path 21 of the light beam 5. In the sample receptacle 9 of the sample receptacle device 2, the fluid sample 3 is introduced into the measurement path 7. By way of example the volume of the introduced fluid sample 3 can be determined on the basis of the measurement path 7. The measurement path 7 accordingly predefines a layer thickness of the fluid sample 3 which the light beam 5 has to pass through in order to reach the light receiver or photosensor 6 from the light source device or illumination device 4.

The spectrometer 1 shown in the exemplary embodiment in FIG. 1 furthermore comprises the microcontroller 34, which is arranged in the housing 31 of the spectrometer 1 and is connected to the analog/digital converter 20. The microcontroller 34 controls the light source device or the illumination device 4 by open-loop and/or closed-loop control. In this case, the microcontroller 34 controls by open-loop and/or closed-loop control for example the light intensity, the light wavelength and/or the luminous duration of the light source device or illumination device 4. The microcontroller 34 is furthermore connectable to the external electronic device 37 for the purpose of transferring the signals of the light receiver or photosensor 6 directly to the electronic device 37, such that the electronic device 37 can evaluate the signals of the light receiver. Additionally or alternatively, the microcontroller 34 can also store the signals of the light receiver 8 in the dedicated storage device 111 as buffer store and they can subsequently be retrieved from the storage device 111 by the electronic device 37. As described above, in this case provision may be made of an analog/digital converter 20 which suitably converts the signals of the light receiver beforehand from an analog signal into a digital signal, for example.

In one embodiment of the spectrometer 1 according to the invention, the microcontroller 34 may be designed for example so as to drive the LEDs 32 of the LED array 33 jointly or instead individually or independently of one another. By way of example, the microcontroller 34 can control the light source device or illumination device 4 depending on the light intensity received by the light receiver 6. For example, if too little light of the light source device or illumination device 4 is received by the light receiver 6, then the light intensity and/or luminous duration can be suitably increased by the microcontroller 34. However, the invention is not restricted to this example. In this regard, alongside the light or illumination intensity or illuminance and the illumination duration, for example an illumination interval can also be controlled by open-loop and/or closed-loop control by the microcontroller 34, depending on function and purpose of use. This applies to all embodiments of the invention.

Furthermore, the microcontroller 34 can additionally or alternatively be designed to be controllable by means of the external electronic device 37 connected to the spectrometer 1 for the purpose of controlling the light source device or illumination device 4 by open-loop and/or closed-loop control, as is indicated by a dashed line in FIG. 1. The measuring apparatus 100 and/or the external electronic device 37 may comprise a control device, such as e.g. the microcontroller 34, for controlling the measuring apparatus 100 by open-loop and/or closed-loop control. In this case, software for controlling the measuring apparatus 100 by open-loop and/or closed-loop control may also be stored in the dedicated storage device 111 thereof and/or be stored by the external electronic device 37, for the purpose of controlling the measuring apparatus 100 by open-loop and/or closed-loop control.

The sample receptacle device 2 received in the housing 31 of the spectrometer 1 is arranged movably in the housing 31 and is provided such that it is retractable into and extendible from the housing 31 in the exemplary embodiment shown in FIG. 1. In this case, the sample receptacle device 2 may optionally additionally be designed to be lockable in different predetermined extended or retracted positions. In this case, the sample receptacle device 2 is designed to be extendible and retractable in a continuously variable manner or in a stepwise manner.

Furthermore, the sample receptacle device 2 designed to be retractable and extendible is received in the housing 31 optionally for example in a light-tight fashion, in a gas-tight fashion and/or in a liquid-tight fashion, such that for example light, gas and/or liquid cannot undesirably penetrate into the housing 31 between the sample receptacle device 2 and the housing 31.

In an alternative embodiment of the spectrometer 1 according to the invention, the sample receptacle device 2 is connected fixedly to the housing 31 or formed integrally with the housing 31.

In the sample receptacle device 2, the sample receptacle 9 is designed in such a way that a fluid sample 3 to be examined by means of the spectrometer 1 is introducible into the sample receptacle 9, wherein the fluid sample 3 is introducible in the measurement path 7 between the photosensor 6 and the light source device or illumination device 4 or an optical waveguide 8 of the sample receptacle device 2.

In the embodiment of the spectrometer 1 as measuring apparatus 100 as shown in FIG. 1, in the sample receptacle device 2 the optical waveguide 8 is optionally additionally arranged in the beam path 21 of the light beam 5 in the longitudinal direction of the sample receptacle device 2. The optical waveguide 8 is for example an acrylic rod, a Macrolon rod, a glass rod, or a fiber-optic cable.

In the exemplary embodiment shown in FIG. 1, the optical waveguide 8 is attached at a first end 14 fixedly in the housing 31 of the spectrometer 1 and is received by the second end 15 in the sample receptacle device 2, which is displaceable along the optical waveguide 8. The optical waveguide 8 can optionally additionally be provided in a manner sealed relative to the sample receptacle device 2, in particular in a liquid-tight fashion and/or in a gas-tight fashion. In this way, if the sample receptacle device 2 is dipped into a liquid to be analyzed, the liquid is prevented from being able to pass undesirably into the interior of the housing 31.

Between the photosensor 6 and the sample receptacle 9, optionally additionally at least one optical device 22, such as a lens 35, for example, is arranged in the sample receptacle device 2. The lens 35 can be provided for example for concentrating or converging the light guided from the light source device 4 through the fluid sample 3 received in the sample receptacle device 2.

The sample receptacle 9 of the sample receptacle device 2 may be designed in such a way that a fluid sample is introducible into the sample receptacle 9 by the sample receptacle device 2 being dipped into the fluid sample, e.g. a liquid and/or a gas. Additionally or alternatively, the sample receptacle 9 may be designed in such a way as to receive a sample container, e.g. a cuvette, having the fluid sample, as is shown by way of example in subsequent FIGS. 2, 3 and 4.

As described above, the light source device or illumination device 4, with its LED array 33 as light source, generates a light beam 5 which is receivable by the photosensor 6 of the sample receptacle device 2. The photosensor 6 is received in a sensor receptacle 13 of the sample receptacle device 2 and converts the impinging light beam 5 into electrical signals and forwards the latter, in the exemplary embodiment in FIG. 1, to the analog/digital converter 20, which converts the electrical signals of the photosensor 6 for example into digital signals and forwards them to the microcontroller 34. The microcontroller 34 in turn transfers the signals to an external electronic device 37 connected to the spectrometer 1 for evaluating the signals and representing the result of the evaluation of the signals, e.g. the concentration of an analyte in a fluid sample. Additionally or alternatively, the signals or data can also be buffer-stored in the storage device 111 of the spectrometer 1 in a manner retrievable for the external electronic device 37.

The analog/digital converter 20 is connected to the photosensor 6, e.g. in a wired fashion, etc., for receiving the signals of the photosensor 6. However, the invention is not restricted to a wired connection of photosensor 6 and converter 20. Any other type of connection can be provided which is suitable for the fact that the converter 20 can receive the signals of the photosensor 6.

The spectrometer 1 comprises at least one connection device 36, for connecting the external electronic device 37, such as, for example, a PC, a tablet PC, server and/or a smartphone, etc., to the spectrometer 1.

By means of the spectrometer 1, the data of the light receiver, e.g. photosensor 6, are transferred to the electronic device 37 for evaluating. The result of the measurement is displayed for example on a display or screen of the electronic device 37.

By means of suitable software, the electronic device 37 performs the evaluation of the signals of the light receiver. The results of the evaluation may subsequently be displayed on a display or screen of the electronic device. Furthermore, the electronic device 37 may optionally additionally control the microcontroller 34 of the spectrometer 1 by means of suitable software and control for example the light source device or illumination device 4 by open-loop and/or closed-loop control by means of the microcontroller 34. This allows a compact design of the spectrometer 1 since the evaluation and display of the results of the evaluation are not carried out by the spectrometer 1 itself, but rather by an external electronic device connectable to the spectrometer 1. Likewise, the external electronic device 37 may also comprise the microcontroller 34 or some other suitable control device for controlling the measuring apparatus 100 by open-loop and/or closed-loop control.

A user of the spectrometer 1 as measuring apparatus 100 can select a measurement program by means of the external electronic device 37. The external electronic device 37 can then correspondingly drive the dedicated microcontroller or the microcontroller 34 of the measuring apparatus 100 to carry out the measurement selected by the user, for example the measurement of the pH value or nitrate content of a sample, etc.

Such measurement programs and other software programs for controlling the measuring apparatus 100 by open-loop and/or closed-loop control may be provided as software, e.g. as app (application software), in a manner loadable onto the external electronic device 37, e.g. a smartphone, a tablet PC, a PC or a server, etc.

Additionally or alternatively, software programs, e.g. measurement programs, etc., via the external electronic device 37, may also be stored on the storage device 111 of the spectrometer 1 in a manner retrievable for the microcontroller 34 of the spectrometer 1.

By means of the connection device 36 of the spectrometer 1, at least one external electronic device 37 can be connected and the data or signals of the photosensor 6 can be transferred to the electronic device 37. In this case, the connection device 36 of the spectrometer 1 may comprise for example a cable connection and/or a wireless connection. The cable connection may be designed for example for connecting a USB cable of a PC, tablet PC, smartphone, laptop, server, etc., wherein the invention is not restricted to such a connection. By way of example, a Bluetooth connection, a radio connection, etc., may be provided as a wireless connection, wherein the invention is not restricted to the abovementioned examples for wireless connections.

As described above, the electronic device 37 has suitable evaluation software for evaluating data or signals of the spectrometer 1 and in particular signals of the light receiver, e.g. photosensor. In this case, the evaluation software can be loaded for example as app (application software) onto the external electronic device 37 and can be used there in the evaluation device 109 for evaluating the data or signals of the spectrometer 1 as measuring apparatus 100. The result of the evaluation of the fluid sample 3 by evaluation of the signals of the light receiver or photosensor 6 in FIG. 1 may, as described above, be displayed, and optionally for example additionally represented graphically, on a display as display device 110 of the electronic device 37. Likewise, the external electronic device 37 may additionally have control software for controlling by open-loop and/or closed-loop control the microcontroller 34 of the spectrometer 1 and/or a dedicated microcontroller in order, via the latter, to control the spectrometer 1 by open-loop and/or closed-loop control.

The evaluation software and the control software may be provided e.g. as evaluation AP or app (evaluation application or evaluation application software) and control AP or app (control application or control application software) for the spectrometer 1 which a user can download via his/her electronic device 37, such as a PC, a tablet PC, a server or a smartphone, for example via the Internet. Afterward, the user can connect his/her electronic device 37 to the spectrometer 1, select a measurement, e.g. measure pH value or measure nitrate content, and cause a fluid sample 3 to be measured by means of the selected measurement and to be evaluated and displayed by his/her electronic device 37 by means of the evaluation software. This has the advantage that the spectrometer 1 can be produced compactly and cost-effectively since, for example, a display for displaying the result of the sample analysis is obviated. Furthermore, it is possible to dispense with a dedicated evaluation device in the spectrometer 1 since to that end an electronic device 37 for evaluation is connected to the spectrometer 1.

The spectrometer 1 may be a spectrometer 1 independent of a power supply system, as is illustrated in FIG. 1, which spectrometer comprises a dedicated energy source 11, e.g. a rechargeable battery and/or a battery. Such a spectrometer 1 can thus be used as a portable spectrometer 1 since, on account of a dedicated energy source 11, it does not require an electricity connection and can thus be taken everywhere to carry out measurements on site. Likewise, the spectrometer 1 may also be a spectrometer dependent on a power supply system, which spectrometer is connectable to an electricity source. For this purpose, the spectrometer 1, by means of its connection device 36 or an additional connection apparatus, not illustrated, is connectable to an energy supply of the electronic device 37 or of some other external energy source and is feedable and/or chargeable with energy of the electronic device 37 or of the external energy device.

As is shown in the exemplary embodiment in FIG. 1, the spectrometer 1 optionally comprises a switch device 38 for switching the spectrometer 1 on and off. By way of example, the light source device or illumination device 4, the photosensor 6 and the microcontroller 34 are switched on and off by means of said switch device 38. Energy can be saved as a result.

As described above, the measurement path 7 of the spectrometer 1 can be set fixedly or be provided in an invariable fashion. In this case, the sample receptacle device 2 is fixedly connected to the housing 31.

Likewise, the measurement path 7 of the spectrometer 1 can be provided in an alterable or variable fashion. For this purpose, the sample receptacle device is arranged in a retractable and extendible fashion in the housing 31 of the spectrometer 1.

As a result, it is possible to determine even analytes with very low or very high concentration in the fluid sample 3. By way of example, the measurement path 7 is chosen to be comparatively large in the case where an analyte is involved which is present in only very low concentration in the fluid sample 3. In this way, a suitably large volume or a suitably large layer thickness of the fluid sample 3 can be provided in the spectrometer 1 and measured by the latter.

In the embodiment of the spectrometer 1 according to the invention as shown in FIG. 1, the measurement path 7 is altered by the sample receptacle device 2 being retracted into and extended from the housing 31. If the sample receptacle device 2 is retracted into the housing 31, as is indicated by a dotted line, then the measurement path 7 is shortened. As a result, a smaller volume or a smaller layer thickness of a fluid sample 3 to be measured is received in the measurement path 7 of the sample receptacle device 2.

By contrast, if the sample receptacle device 2 is extended from the housing 31, then the measurement path 7 and accordingly the cross section of the sample receptacle 9 are enlarged and a larger volume or a larger layer thickness of a fluid sample 3 to be measured can be received in the measurement path 7 of the sample receptacle device 2. In this case, in one embodiment of the spectrometer 1 according to the invention, the optical waveguide 8 received in the beam path of the sample receptacle device 2 may preferably additionally be sealed relative to the sample receptacle device 2, in particular in a liquid-tight fashion and/or in a gas-tight fashion, in order to prevent the fluid sample 3 from penetrating into the housing 31 of the spectrometer 1.

Likewise, in a further embodiment of the invention, provision may be made of sample containers having cross sections of different sizes for being received in the sample receptacle 9 of the sample receptacle device 2. If the measurement path 7 and accordingly the cross section of the sample receptacle 9 are reduced, for example, as is indicated by a dotted line in FIG. 1, then a sample container having a cross section reduced in accordance with the sample receptacle 9 and having a fluid sample 3 received therein can be inserted into said sample receptacle. In this case, an additional sealing of the optical waveguide 8 relative to the sample receptacle device 2 can be dispensed with.

In an alternative embodiment, not illustrated, of the spectrometer 1 according to the invention as measuring apparatus, no additional optical waveguide 8 is provided in the sample receptacle device 2. Instead, the measurement path 7 is provided directly between the photosensor 6 and the light source device or illumination device 4. In this case, the measurement path 7 is likewise altered by the sample receptacle device 2 being arranged in a retractable and extendible fashion in the housing 31 of the spectrometer 1. Likewise, sample containers having different cross-sectional sizes can be used and inserted into the correspondingly enlarged or reduced sample receptacle cross section of the sample receptacle device 2, as described above.

Figure 2:
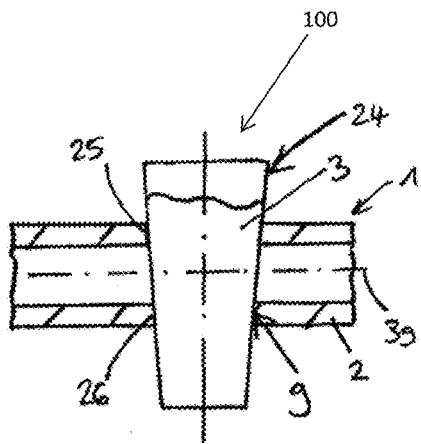
FIG. 2 shows an excerpt from one exemplary embodiment of a sample receptacle device and its receptacle and a sample container—received in the receptacle—of a spectrometer according to the invention as measuring apparatus.

FIG. 2 shows an excerpt from a sample receptacle 9 of a sample receptacle device 2 in accordance with one embodiment of a spectrometer 1 according to the invention as measuring apparatus 100. A sample container 24 having a fluid sample 3 for analysis by the spectrometer 1 is arranged in the sample receptacle 9. In this case, the sample receptacle 9 is shown in a cross-sectional view in the longitudinal direction of the sample receptacle device 2. The longitudinal axis 39 of the sample receptacle device 2 is furthermore depicted. The arrangement of the light receiver is not shown in FIG. 2 and the subsequent FIGS. 3 and 4, for reasons of clarity.

As is shown in FIG. 2, the sample receptacle 9 is open on both sides of the sample receptacle device 2 for leading through for example a sample container 24 in the transverse direction through the sample receptacle device 2. For this purpose, the sample receptacle 9 of the sample receptacle device 2 has a respective opening 25, 26 at both opposite sides, wherein the openings 25, 26 in this case taper for example in their cross section in such a way that a sample container 24 having a correspondingly tapering cross section can be inserted therein and held in the sample receptacle 9, as is shown in the exemplary embodiment in FIG. 2.

Figure 3:
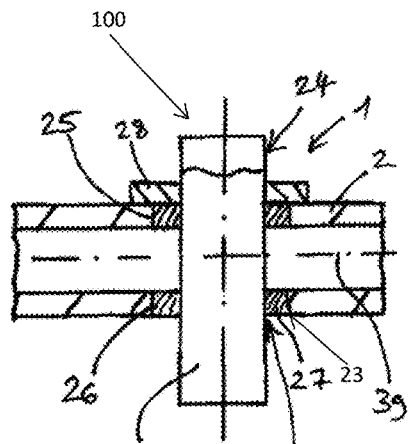
FIG. 3 shows an excerpt from a further exemplary embodiment of a sample receptacle device and its receptacle and a sample container—received in the receptacle—of a spectrometer according to the invention as measuring apparatus.

The openings 25, 26 can optionally additionally be provided in each case with an additional sealing device, not illustrated, for tightly connecting sample receptacle 9 and sample container 24, as is shown by way of example in subsequent FIG. 3. The sealing device is designed so as to connect the sample receptacle 9 and the sample container 24 in particular in a gas-tight, liquid-tight and/or light-tight fashion.

Furthermore, FIG. 3 shows an excerpt from a sample receptacle 9 of a sample receptacle device 2 in accordance with a further exemplary embodiment of the spectrometer 1 according to the invention as measuring apparatus 100. In this case, the sample receptacle 9 and the sample container 24 received therein and having a fluid sample 3 are shown in a cross-sectional view in the longitudinal direction of the sample receptacle device 2.

As is shown in FIG. 3, the sample receptacle 9 of the sample receptacle device 2 has a respective opening 25, 26 at both opposite sides, wherein the openings 25, 26 in this case have the same cross section, such that a sample container 24 having a corresponding cross section can be inserted into the receptacle 9. In the exemplary embodiment shown in FIG. 3, the sample receptacle 9 has for example two circular openings 25, 26 for receiving a cylindrical sample container 24.

For holding a sample container 24 in the receptacle 9, the receptacle 9 and/or the sample container 24 may be provided for example with an elastic section 27 or elastic ring, e.g. composed of rubber and/or foamed material, for holding the sample container 24 in the sample receptacle 9 after it has been inserted into the sample receptacle 9.

The elastic section 27 of the sample receptacle 9 can be compressed upon insertion of the sample container 24 and prevents the sample container 24 from undesirably slipping out of the sample receptacle 9. Optionally, the elastic section 27 may also additionally be designed as a sealing device 23, for additionally sealing the sample container 24 relative to the sample receptacle 9, and in particular sealing the sample container 24 relative to the sample receptacle 9 in a gas-tight, liquid-tight and/or light-tight fashion, such that no gas, no liquid and/or no light can pass between the sample container 24 and the sample receptacle 9 through the elastic section 27 into the sample receptacle device 2.

Additionally or alternatively, the sample container 24 may also be equipped with a collar 28, e.g. an elastic or rigid collar, and/or be formed with a flange (not illustrated), with which collar or flange the sample container 24 can bear on the top side of the sample receptacle 9. In this way, it is likewise possible to prevent the container 24 from undesirably slipping out of the sample receptacle 9. Moreover, it is possible as necessary to provide an additional sealing device between the sample receptacle 9 and the sample container 24.

Figure 4:
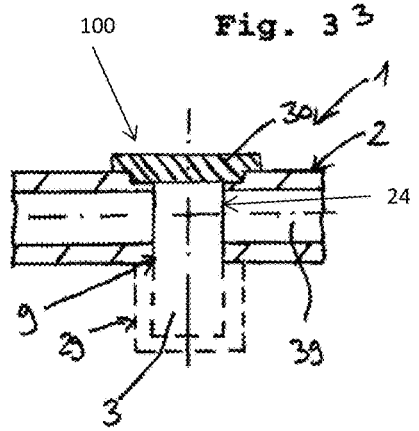
FIG. 4 shows an excerpt from another exemplary embodiment of a sample receptacle device and its receptacle and a sample container—received in the receptacle—of a spectrometer according to the invention as measuring apparatus.

FIG. 4 shows an excerpt from a sample receptacle 9 of a sample receptacle device 2 in accordance with another exemplary embodiment of the spectrometer 1 according to the invention as measuring apparatus 100. In this case, the sample receptacle 9 is shown in a cross-sectional view in the longitudinal direction of the sample receptacle device 2.

As is shown in FIG. 4, the sample receptacle 9 forms a depression 29 for receiving a sample container 24 having a fluid sample 3. In this case, the length of the depression 29 can be determined by the sample receptacle device 2 or the sample receptacle device 2 can be formed in a manner additionally recessed in the region of the receptacle 9, for receiving a sample container 24, as is indicated by a dashed line in FIG. 4. Additionally, the receptacle 9 and/or the sample container 24 may be designed to be closeable with a cover 30, in particular in a gas-tight, liquid-tight and/or light-tight fashion.

The sample receptacle device of the spectrometer 1 according to the invention as measuring apparatus 100 described above with reference to FIGS. 1 to 4 may optionally and additionally be produced from a for example acid-resistant material if a fluid sample to be measured is an acid or is acid-containing. This applies to all embodiments of the invention.

The external electronic device 37 described above with reference to FIG. 1 forms an external evaluation and display apparatus for evaluating the information or signals of the light receiver 6 of the spectrometer and for displaying the result or the results of the evaluation of the measurements of the spectrometer.

The spectrometer 1 itself in turn only forms a measuring apparatus comprising the devices required for the measurement of the fluid sample, such as e.g. the light source device or illumination device 4, the light receiver 6, the sample receptacle device 2, the microcontroller 34 and the converter 20.

The separation of the evaluation of the measurements of the spectrometer and the display of a respective result of the evaluation from the spectrometer and the limitation of the spectrometer to the measurement and the devices required therefor, such as e.g. the light source device and the light receiver, enable the spectrometer as measuring apparatus 100 to be constructed in a small and compact fashion.

Figure 5:
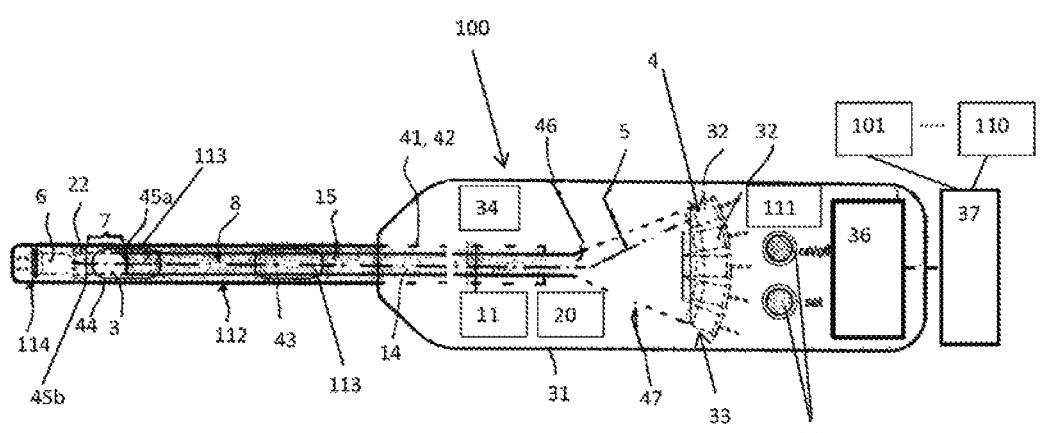
FIG. 5 shows a further exemplary embodiment of a spectrometer as measuring apparatus according to the invention.

FIG. 5 shows one exemplary embodiment of the spectrometer 1 as measuring apparatus 100 in accordance with FIGS. 1-4 described above. In this case, the spectrometer 1 in FIG. 5 comprises an extendible measurement path 7. The explanations concerning the spectrometer which were given above with reference to FIGS. 1-4 correspondingly also apply to the spectrometer 1 shown in FIG. 5. Therefore, reference is made to the explanations concerning FIGS. 1-4 in order to avoid unnecessary repetitions.

The spectrometer 1 as measuring apparatus 100 in FIG. 5 comprises a plurality of light sources as light source device or illumination device. The light sources are preferably LEDs 32, with further preference laser LEDs. The light sources are designed to emit almost monochromatic light having a wavelength of preferably 250-750 nm. The light sources are preferably designed to emit in each case light of different wavelengths or in different wavelength ranges. By way of example, one light source may be designed to emit light having a wavelength of between 610 and 750 nm and the other light source may be designed to emit light having a wavelength of between 590 and 610 nm. The choice of the respective light source may depend on the fluid sample 3 and/or the analyte concentration needing to be measured and may also be selected automatically.

The one or the plurality of light sources generate a light beam 5, which is indicated in a dash-dotted fashion in FIG. 5. The plurality of light sources may be arranged approximately semicircularly and with further preference may form an array 33.

The spectrometer 1 as measuring apparatus 100 furthermore comprises a photosensor 6 for receiving the light beam 5. The photosensor 6 converts the impinging light beam 5 into electrical signals or data. The electrical signals or data depend in each case on the impinging light power and/or wavelength of the light beam 5. The photosensor 6 is preferably a photodiode.

Furthermore, the spectrometer 1 is designed with a measurement path 7 in the beam path of the light beam 5. The fluid sample 3 is introducible into the measurement path 7. The measurement path 7 is provided in a variable fashion. For this purpose, the spectrometer 1 is designed for example as follows:

An optical waveguide 8, for example in the form of an acrylic rod, Macrolon rod, glass rod or fiber-optic cable, is arranged in the beam path of the light beam 5.

The optical waveguide 8 has a first section 14, which is accommodated fixedly in a handling part designed as a housing 31. The optical waveguide 8 furthermore has a second section 15, which extends out of the housing 31 into a sleeve 112.

The sleeve 112 has a substantially ring-shaped cross section. The internal diameter of the ring-shaped cross section of the sleeve 112 substantially corresponds to the external diameter of the circular cross section of the optical waveguide 8.

The sleeve 112 is preferably provided with a plurality of elongate holes 113. In this case, as shown in FIG. 5, two elongate holes 113 in each case may be opposite one another. Furthermore, by way of example, two of such pairs of opposite elongate holes 113 may be provided in a manner spaced apart from one another along the sleeve 112 along the beam path of the light beam 5. Independently of the position of the sleeve 112 in relation to the housing 31 or the optical waveguide 8, one of the elongate holes 113 is always connected to the measurement path 7, that is to say that the fluid sample 3 can be taken from the fluid, for example a stretch of water. In accordance with the present exemplary embodiment, such sampling can be performed in a simple manner by dipping the elongate holes 113, that is to say thus also dipping the sleeve 112 together with the end piece 114, into the fluid.

The sleeve 112 has a first section 41, by which it extends into the housing 31. The section 41 is received movably along the beam path of the light beam 5 in the housing 31 in a receptacle space 42 thereof. By way of example, the section 41 can be provided with an external thread which engages into a corresponding internal thread in the housing 31. Alternatively, the section 41 can be provided on the outer side with catches which engage with corresponding mating catches in the housing 31 and thus allow a stepwise displaceability of the sleeve 112 relative to the housing 31. However, the invention is not restricted to the examples mentioned.

A second section 43 of the sleeve 112 extends toward the outside out of the housing 31 and in this case surrounds the second section 15 of the optical waveguide 8. Adjacent to the second section 43 of the sleeve 112 is a third section 44 of the sleeve 112, which third section delimits the fluid sample 3 at the circumference thereof. The end piece 114 is in turn adjacent to the third section 44. The end piece 114 closes the ring-shaped cross section of the sleeve 112 in a fluid-tight fashion.

The measurement path 7 is thus defined between the front end 45b of the end piece and an end side 45a of the optical waveguide 8.

The end piece 114 has the photosensor 6 and optionally an additional lens 22 as one example of an optical device, which concentrates e.g. the incident light beam 5 onto the photosensor 6. Further examples of optical devices alongside a lens are e.g. mirrors and prisms. However, the invention is not restricted to the examples mentioned. Such optical devices 22 can be used in all embodiments of the invention, such as are described by way of example in FIGS. 1-9, and be used for concentrating, converging, guiding and/or scattering light of, for example, the light source device or illumination device and of a luminescent sample described below.

By virtue of the fact, then, that the sleeve 112 is moved into the receptacle region or receptacle space 42 of the housing 31 or is moved out of the receptacle region or receptacle space 42 of the housing 31, the measurement path 7 is set and can thus be adapted to the requirements for a concentration measurement of a respective analyte in a simple manner. It is also conceivable here for the sleeve 112 to be moved into the housing 31 and out of the housing 31 in an automated manner, for example by means of a corresponding servomotor.

The light beam 5 is coupled in at the other end side 46 of the optical waveguide 8. In this case, means 47 may be provided for optionally connecting one or the other light source, here LED 32, to the optical waveguide 8 in a light-guiding manner.

Furthermore, the spectrometer 1 may optionally comprise an additional microcontroller 34 and/or be couplable to such a microcontroller of an external device 37. Likewise, the spectrometer 1 as measuring apparatus 100, as described above, may optionally additionally comprise at least one dedicated storage device 111, an energy source 11, an analog/digital converter 20 and/or a switch device 38 for switching on and off the spectrometer 1 as measuring apparatus 100.

The spectrometer 1 as measuring apparatus 100 comprises, as above the spectrometer described with reference to FIGS. 1-4, at least one connection device 36, for connecting an external electronic device 37, such as, for example, a PC, a tablet PC, a server and/or a smartphone, etc. In this case, the connection device 36 is a cable connection, e.g. a USB cable connection, etc., and/or a wireless connection, e.g. a Bluetooth connection or radio connection, etc.

By means of the spectrometer 1 as measuring apparatus 100, as described above, the data or signals of the photosensor 6 as light receiver are transferred to the electronic device 37 for evaluation by an evaluation device 109. The result of the measurement is displayed for example on a display device 110 such as e.g. a display or screen of the electronic device 37. By means of suitable software, the electronic device 37 performs the evaluation of the signals of the light receiver.

Furthermore, the electronic device 37 may optionally additionally control the microcontroller 34 of the spectrometer 1 by means of suitable software and control for example the light source device or illumination device 4 and/or the photosensor 6 by open-loop and/or closed-loop control by means of the microcontroller 34.

The external electronic device 37, for example a smartphone, a PC, a server or a tablet PC, etc., comprises, as was described above with reference to FIGS. 1-4, a GPS device 101, a time measuring device 102, a camera device 103, a storage device 104, a transmitting device 105, a receiver device 106, a scanner device 107 and/or a microphone device 108, which may be used together with the measuring apparatus 100, as described above.

Figure 6:
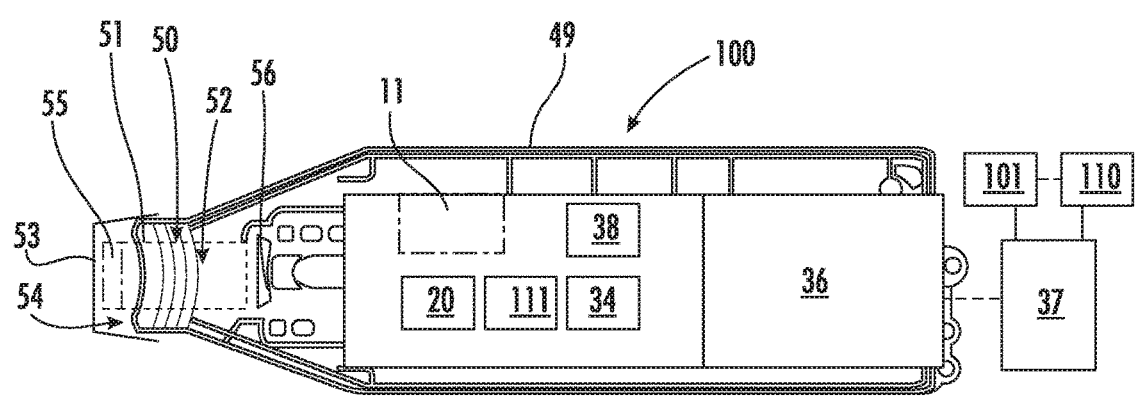
FIG. 6 shows one exemplary embodiment of a measuring apparatus according to the invention, wherein the measuring apparatus measures or analyzes a luminescent sample, wherein part of the housing has been removed from the measuring apparatus.
Figure 7:
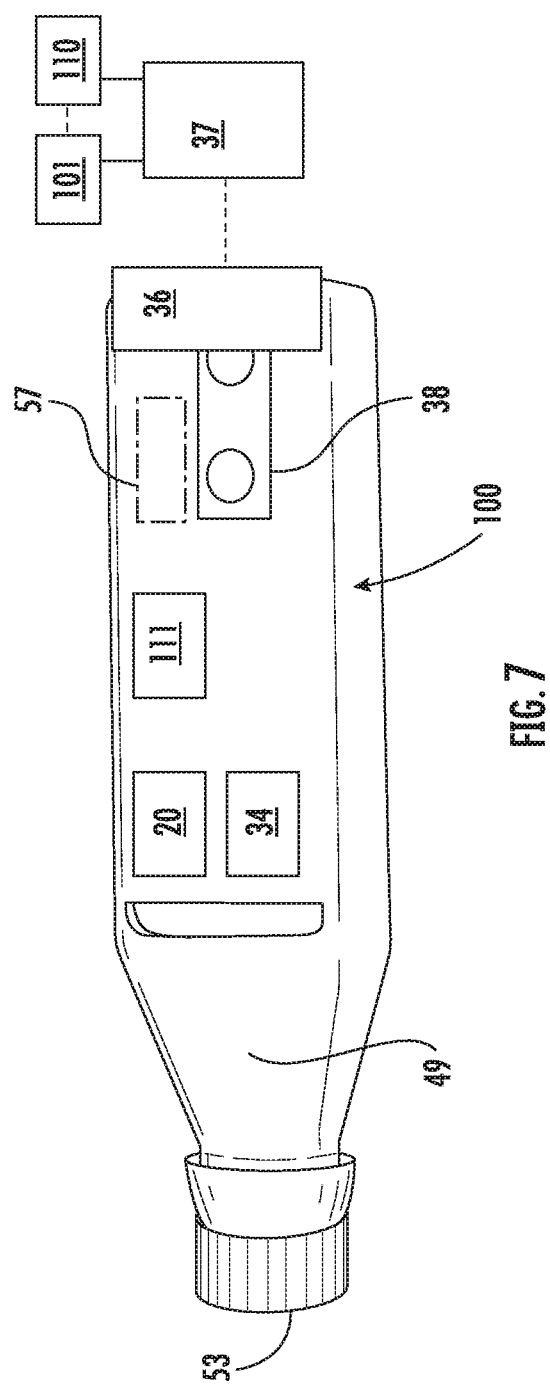
FIG. 7 shows the measuring apparatus in accordance with FIG. 6 and its housing.

A further exemplary embodiment of a measuring apparatus 100 is shown in subsequent FIGS. 6 and 7. FIGS. 6 and 7 show the measuring apparatus 100 in a plan view, wherein a part of the housing 49 has been removed in FIG. 6.

The measuring apparatus 100 shown in FIGS. 6 and 7 is designed here in such a way that luminescent samples can be measured or analyzed.

Luminescence is the optical radiation of a physical system that arises upon transition from an excited state to the ground state. The cause here is radiative deactivation.

Depending on the type of excitation, a distinction is drawn between different types of luminescence, including for example so-called photoluminescence, so-called chemoluminescence and so-called bioluminescence.

In the case of photoluminescence, excitation of the system is effected by photons. In this case, a distinction is drawn between phosphorescence and fluorescence depending on the time duration between excitation and emission of the light. Fluorescence is the spontaneous emission of light shortly after the excitation of a material. Phosphorescence is in turn the property of a substance to persistently glow in the dark after illumination with light, for example with visible light or UV light. The cause is radiative deactivation.

In the case of chemoluminescence, the excitation of the system is effected by a chemical reaction. By way of example, in this case luminol can be used for detecting blood.

In the case of bioluminescence, the excitation of the system is effected by a chemical reaction in a living organism, for example a cell, a bacterium or an animal, such as a firefly, for example, in which luciferin is oxidized.

For analyzing a luminescent sample, the measuring apparatus 100 comprises in the housing 49 a sample receptacle space 50, into which a sample container 51 having the luminescent sample 52 is introducible and analyzable. In this case, the sample container 51 is closeable, in particular tightly closeable, by means of a cover, for example, such that the sample cannot undesirably escape from the sample container 51.

In this case, the sample container 51 is transparent, for example composed of a transparent plastic or a transparent glass, for transmitting the radiation, e.g. visible light, emitted by the luminescent sample 52, and if appropriate for transmitting radiation of at least one additional illumination device 55 for illuminating the luminescent sample 52, in order to excite the latter to persistently glow.

In this case, the sample container 51 may be integrated fixedly or releasably in the housing 31. If the sample container 51 is integrated releasably in the housing 49, then it can easily be removed from the housing 49 through a corresponding housing opening 54, be filled with the luminescent sample 52 and then inserted into the housing 49. In the case where the sample container 51 is integrated fixedly in the housing 49, the cover can be removed for the purpose of filling the sample container and, after the sample container 51 has been filled, said cover can close the latter again. The cover, just like the sample container 51, can be designed to be transparent or else be opaque, depending on whether e.g. an additional illumination device 55 is used and where the latter is arranged.

The housing opening 54 for inserting and/or filling the sample container 51 is preferably designed to be closeable, in particular designed to be closeable in a light-tight fashion, with a cover element, e.g. a closure cap 53. In this way, it is possible to ensure that no light from outside can penetrate into the housing 49 and the sample receptacle space 50 thereof and corrupt the measurement result.

In the housing 49, preferably in the sample receptacle space 50 of the housing 49, at least one radiation receiver device 56 is furthermore provided, for receiving the radiation emitted by the luminescent sample 52 and converting it into electrical signals. By way of example, a light sensor or photosensor may be used as radiation receiver device 56 for receiving radiation, such as e.g. light, etc., of the luminescent sample 52. In this case, the photosensor may comprise at least one photodiode. Instead of a light sensor or photosensor, any other suitable radiation receiver device or combination of radiation receiver devices may also be provided which is suitable for receiving the radiation emitted by a luminescent sample, such as e.g. light, etc.

In the housing 49 the at least one additional illumination device 55 may optionally additionally furthermore be provided for analyzing a photoluminescent sample as an example of a luminescent sample 52. By means of the illumination device 55, the luminescent sample 52 is illuminated with a suitable radiation for exciting the luminescent sample 52 to persistently glow. Such luminescent or photoluminescent samples are for example fluorescent samples or phosphorescent samples. In this case, the illumination device 55 is likewise arranged e.g. in the sample receptacle space 50, as is indicated by a dashed line in FIG. 6. By way of example, the illumination device 55 may also be integrated into the cover of the sample container 51 or be arranged at any other location of the sample receptacle space 50 that is suitable for a measurement.

By way of example, a plurality of illumination devices 55 may be provided, wherein the illumination devices 55 all emit light of the same wavelength or light of different wavelengths for illuminating the luminescent sample 52. As a result, a luminescent sample 52 to be examined can be illuminated, for example alternatively, with light of a different wavelength in order to determine e.g. a plurality of or different analytes.

The measuring apparatus 100 is connectable to an external electronic device 37 by means of at least one connection device 36, wherein the connection device 36 has a cable connection and/or a wireless connection. The cable connection may, as described above with reference to FIGS. 1-5, be designed for example for connecting a USB cable of a PC, tablet PC, smartphone, laptop, server, USB stick, etc., wherein the invention is not restricted to such a connection. By way of example, a Bluetooth connection, a radio connection, etc., may be provided as a wireless connection, wherein the invention is not restricted to the abovementioned examples for wireless connections.

The external electronic device 37, such as, for example, a smartphone, a server or a tablet PC, etc., may, as was described above with reference to FIGS. 1-5, comprise a GPS device 101, a time measuring device 102, a camera device 103, a storage device 104, a transmitting device 105, a receiver device 106, a scanner device 107 and/or a microphone device 108, which may be used together with the measuring apparatus 100.

Optionally, the measuring apparatus 100 may furthermore itself comprise at least one dedicated storage device 111 for storing or buffer-storing for example the measurement data or measurement signals, etc. In this case, the storage device 111 can be accessed by the external electronic device 37.

Furthermore, the radiation receiver device 56 of the measuring apparatus 100 may be connected to an evaluation device 109 of the external electronic device 37 and the signals or data of the radiation receiver device 56 may be transferred to the evaluation device 109 wirelessly or in a wired fashion. In this case, by way of example, the signals or data of the radiation receiver device 56 are evaluated for analyzing the luminescent sample 52 in the evaluation device 109 of the external electronic device 37. Furthermore, the results of the evaluation can be displayed on a display device 110, e.g. a display or screen, of the external electronic device 37. Likewise, the data or signals of the measuring apparatus 100 can also be stored in the storage device 104 of the external electronic device 37.

Furthermore, the spectrometer 1, as described above, may optionally comprise an additional microcontroller 34 and/or be couplable to such a microcontroller of an external device 37.

The microcontroller 34 may be used for example for controlling the illumination of the respective illumination device 55 by open-loop and/or closed-loop control and/or for controlling the sensitivity of the radiation receiver device 56 by open-loop and/or closed-loop control, etc. By way of example, the microcontroller 34 can control by open-loop and/or closed-loop control the illumination duration, the illuminance, the illumination interval of the illumination device 55, etc. However, the invention is not restricted to the examples mentioned. By means of the microcontroller 34, furthermore, a plurality of illumination devices 55 may also be driven jointly or independently of one another for analyzing a luminescent sample 52 in the sample receptacle space 50 of the measuring apparatus 100.

Likewise, the measuring apparatus 100, as described above, may optionally additionally comprise at least the dedicated storage device 111, an energy source 11, an analog/digital converter 20 and/or a switch device 38 for switching the measuring apparatus 100 on and off.

Moreover, the sample receptacle space 50 may additionally be designed to be closeable in a light-tight fashion or shielded from ambient light in the housing 49 of the measuring apparatus 100, such that apart from light of a possibly additionally present illumination device 55 for the targeted illumination of the luminescent sample 52 in the sample receptacle space 50 no light from outside the housing 49 of the measuring apparatus 100 or else, if present, from light sources within the housing 49 can penetrate undesirably into the sample receptacle space 50 and into the sample 52 contained there.

FIG. 7 shows the measuring apparatus 100 in accordance with FIG. 6 and its housing 49. As described above with reference to FIG. 6, the housing opening 54 for inserting and/or filling the sample container 51 is preferably tightly closed, in particular at least in a light-tight fashion, with a cover element, e.g. a closure cap 53 in FIG. 7. In the case of light-tight closure of the housing opening, no light from outside penetrates undesirably into the housing 49. As described above with reference to FIG. 6, the sample receptacle space within the housing 49 may likewise additionally be designed to be light-tight or shielded from ambient light. In this way, for example, a sample is illuminated only by an additional illumination device 55 present, but is not illuminated undesirably by further luminous devices possibly present in the interior of the housing.

As shown in FIG. 7, the measuring apparatus 100 may be designed as a portable measuring apparatus 100 and comprise the dedicated energy source 11 mentioned above, as is indicated by a dash-dotted line in FIG. 7, for feeding devices such as e.g. an illumination device 55 and/or the radiation receiver device 56 with energy. In this case, the energy source 11 is for example a battery device and/or a rechargeable battery. By means of the connection device 36, e.g. a cable connection, for example an external energy source may be connected in order to supply the measuring apparatus 100 with energy.

In one embodiment of the measuring apparatus in accordance with FIGS. 6 and 7, the cover element 53 for closing the housing opening may simultaneously be designed for closing the sample container 51, such that the separate cover for the sample container may be obviated.

The measuring apparatus 100 described by way of example above with reference to FIGS. 6 and 7 may analyze, as luminescent sample, solid, liquid, pasty, pulverulent and/or gaseous samples and also organisms, cells, animals, such as, for example, insects, etc., provided that they are luminescent.

Figure 8:
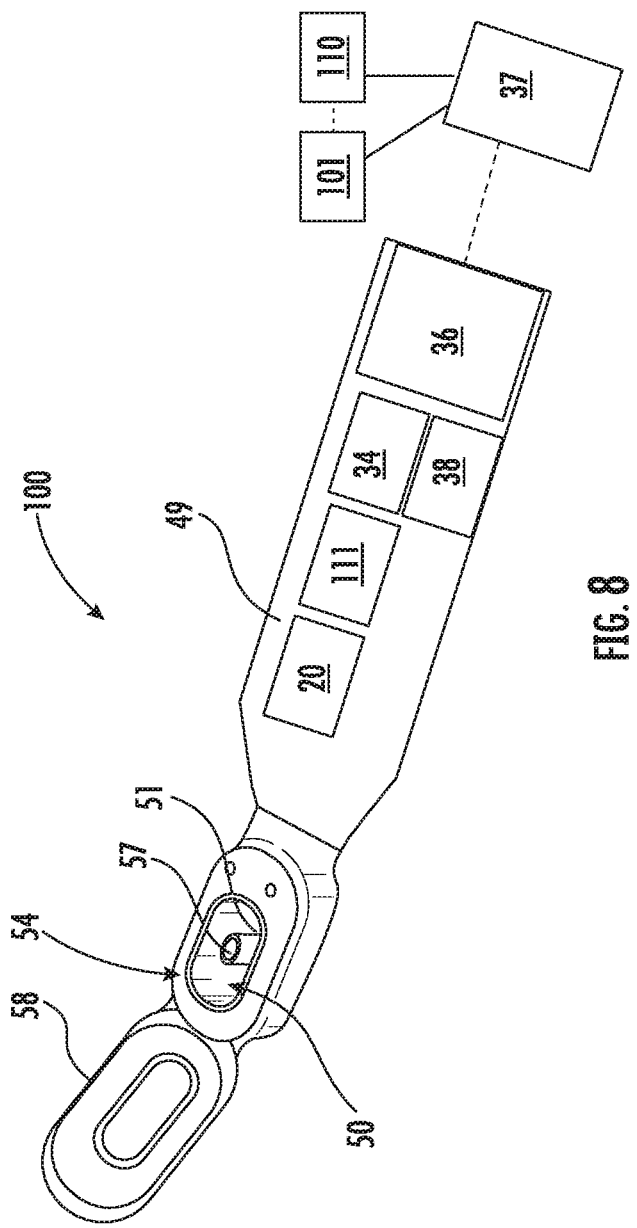
FIG. 8 shows a further exemplary embodiment of a measuring apparatus for measuring or analyzing a luminescent sample.

FIG. 8 shows one exemplary embodiment of a measuring apparatus 100 which, like the measuring apparatus in FIGS. 6 and 7, is designed so as to measure or to analyze luminescent samples. In this case, the measuring apparatus 100 in accordance with FIG. 8 has substantially the same construction as the measuring apparatus in accordance with FIGS. 6 and 7, and so reference is made to the description in FIGS. 6 and 7 in order to avoid unnecessary repetitions.

The measuring apparatus 100 comprises, for analyzing a luminescent sample, a housing 49 having a sample receptacle space 50, into which a sample container 51 having the luminescent sample is introducible and analyzable. In this case, the sample container 51 is closeable, in particular tightly closeable, for example by means of a cover 57, such that the sample cannot undesirably escape from the sample container 51.

In this case, the sample container 51 is transparent for transmitting the radiation emitted by the luminescent sample, and if appropriate for transmitting radiation of at least one additional illumination device for illuminating the luminescent sample in order to excite the latter to persistently glow.

In this case, the sample container 51 may be integrated fixedly or releasably in the housing 49. If the sample container 51, e.g. a glass vial, is integrated releasably in the housing 49, then it can easily be removed from the housing 49 through a corresponding housing opening 54 of the housing 49, be filled with the luminescent sample and then inserted into the housing again. In the case where the sample container 51 is integrated fixedly in the housing 49, the cover 57 can be removed for the purpose of filling the sample container 51 and can close the sample container 51 again after the latter has been filled. The cover, just like the sample container, may be designed to be transparent or else opaque or partly opaque.

The housing opening 54 of the housing 49 for inserting and/or filling the sample container 51 is designed to be closeable, in particular designed to be closeable in a light-tight fashion, with a cover element, e.g. a closure flap 58 or a closure cap not illustrated. In this case, the closure flap 58 is pivotably secured to the housing 49 of the measuring apparatus 100, as is shown in the exemplary embodiment in FIG. 8.

In this way, it can be ensured that no light from outside can penetrate into the housing 49 and the sample receptacle space 50 thereof and corrupt the measurement result.

In the sample receptacle space 50 of the measuring head, provision is furthermore made of at least one radiation receiver device, for example, for receiving the radiation emitted by the luminescent sample and converting it into electrical signals. By way of example, a light sensor, photomultiplier, avalanche diodes or photosensor may be used as radiation receiver device for receiving radiation, such as e.g. light, etc., of the luminescent sample. In this case, the photosensor may comprise at least one photodiode. Instead of a light sensor, photomultiplier, avalanche diodes or photosensor, it is also possible to provide any other suitable radiation receiver device or combination of radiation receiver devices suitable for receiving the radiation emitted by a luminescent sample, such as e.g. light, etc.

In the housing 49 the at least one additional illumination device may optionally additionally furthermore be provided for analyzing a photoluminescent sample as an example of a luminescent sample. By means of the illumination device, the luminescent sample is illuminated with a suitable radiation for exciting the luminescent sample to persistently glow. Such luminescent or photoluminescent samples are for example fluorescent samples or phosphorescent samples. In this case, the illumination device is likewise arranged e.g. in the sample receptacle space 50.

By way of example, a plurality of illumination devices may be provided, wherein the illumination devices all emit light of the same wavelength or light of different wavelengths for illuminating the luminescent sample.

The measuring apparatus 100 is connectable to an external electronic device 37 by means of at least one connection device 36, wherein the connection device 36 has a cable connection and/or a wireless connection. The cable connection may, as described above with reference to FIGS. 1-7, be designed for example for connecting a USB cable of a PC, tablet PC, smartphone, laptop, server, USB stick, etc., wherein the invention is not restricted to such a connection. By way of example, a Bluetooth connection, a radio connection, etc., may be provided as a wireless connection, wherein the invention is not restricted to the abovementioned examples for wireless connections.

The external electronic device 37, such as, for example, a smartphone, a server or a tablet PC, etc., may comprise a GPS device 101, a time measuring device 102, a camera device 103, a storage device 104, a transmitting device 105, a receiver device 106, a scanner device 107 and/or a microphone device 108, which may be used together with the measuring apparatus 100.

Optionally, the measuring apparatus 100 may furthermore itself comprise at least one dedicated storage device 111 for storing or buffer-storing for example the measurement data or measurement signals, etc. In this case, the storage device 111 can be accessed by the external electronic device 37.

Furthermore, the radiation receiver device of the measuring apparatus 100 may be connected to an evaluation device 109 of the external electronic device 37 in order to transfer the signals or data of the radiation receiver device the evaluation device 109 wirelessly or in a wired fashion. In this case, by way of example, the signals or data of the radiation receiver device are evaluated for analyzing the luminescent sample in the evaluation device 109 of the external electronic device 37. Furthermore, the results of the evaluation can be displayed on a display device 110, e.g. a display or screen, of the external electronic device 37. Likewise, the data or signals of the measuring apparatus 100 can also be stored in a storage device 104 of the external electronic device 37.

Furthermore, the measuring apparatus 100, as described above, may itself optionally comprise an additional microcontroller 34 and/or be couplable to such a microcontroller of an external device 37. The microcontroller 34 may be used for example for controlling the illumination of the respective illumination device by open-loop and/or closed-loop control and/or for controlling the sensitivity of the radiation receiver device by open-loop and/or closed-loop control, etc. By way of example, the microcontroller 34 can control by open-loop and/or closed-loop control the illumination duration, the illuminance, the illumination interval of the illumination device, etc. However, the invention is not restricted to the examples mentioned. This applies to all embodiments of the invention. By means of the microcontroller 34, furthermore, a plurality of illumination devices may also be driven jointly or independently of one another for analyzing a luminescent sample in the sample receptacle space 50 of the measuring apparatus 100.

Likewise, the measuring apparatus 100, as described above, may optionally additionally comprise, besides the at least one dedicated storage device 111, an energy source 11, an analog/digital converter 20 and/or a switch device 38 for switching the measuring apparatus 100 on and off.

Figure 9:
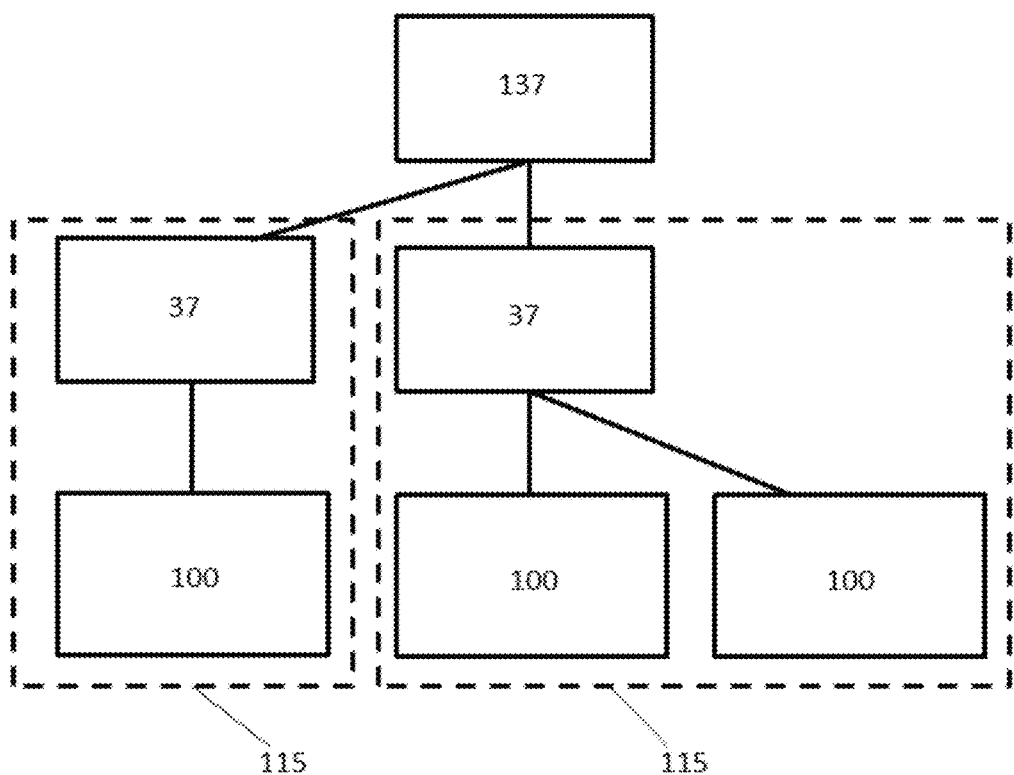
FIG. 9 shows a diagram of a measurement system in accordance with one embodiment of the invention.

FIG. 9 illustrates a diagram of a measurement data system. In this case, the measurement data system comprises a first electronic device 137, for example a server, a PC, a smartphone or a tablet PC, a plurality of second electronic devices 37, in particular smartphones or tablet PCs, and a plurality of measuring apparatuses 100. In this case, the first electronic device 137 is connectable to the second electronic devices 37 wirelessly and/or in a wired fashion, as was described above by way of example with reference to the exemplary embodiment in FIG. 1, and forms therewith a measuring and evaluation apparatus 115. In this case, the second electronic device 37 comprises a receiver device for receiving data or signals etc. of the measuring apparatus 100 and of the second electronic device 137. Furthermore, the second electronic device 37 can transfer data or signals etc. by means of its transmitting device to the measuring apparatus 100 and the first electronic device 137.

The second electronic devices 37 are in each case connectable to one or a plurality of assigned measuring apparatuses 100 wirelessly and/or in a wired fashion as was likewise described above with reference to the exemplary embodiment in FIG. 1 and the exemplary embodiments in FIGS. 2-8.

The measuring apparatuses 100 are designed as spectrometer or measuring apparatus for measuring or analyzing luminescent samples. Such measuring apparatuses 100 were described above on the basis of the exemplary embodiments in FIGS. 1-8.

By means of the respective measuring apparatus 100, a sample is measured or analyzed on site, for example a water sample at a well in Africa. The measurement data, for example analog and/or digital signals of the measuring apparatus 100, are transferred from the measuring apparatus 100 to the assigned second electronic device 37 and received by the receiver device thereof, for example wirelessly by means of a Bluetooth or radio interface or in a wired fashion by means of e.g. a USB interface.

The second electronic device 37 can evaluate the measurement signals for example in its evaluation device and transfer them to the first electronic device 137, for example a central server in Germany, e.g. wirelessly, e.g. by means of a radio interface via a satellite. The second electronic device 37 comprises, for wireless reception and transfer, the receiver device and the transmitting device, as was described above with reference to FIGS. 1-8.

The first or superordinate electronic device 137 can store the results of the evaluation of the measuring apparatus 100 and use them further in order for example to manage, test, evaluate the latter, etc. Furthermore, the results of the evaluation or test can be retrieved worldwide from the central server for example by other electronic devices e.g. in environmental authorities.

As was described above with reference to FIGS. 1-8, the second electronic device 37 may not only evaluate the signals or measurement signal of the measuring apparatus in its evaluation device, but in addition or as an alternative to the evaluation device may comprise a GPS device, a time measuring device, a camera device, a storage device, a scanner device, a display device, a transmitting device, a receiver device and/or a microphone device, which may be used jointly with the measuring apparatus 100.

As a result, alongside the measurement data, in particular the analog and/or digital signals of the measuring apparatus, further information or data may be assigned to the GPS device, the time measuring device, the camera device, the scanner device, and/or the microphone device, etc., and may be transferred to the first or superordinate electronic device, for example by means of the transmitting device.

In this regard, e.g. the geographical position of a measurement carried out by the measuring apparatus 100 may be determined by the GPS device and concomitantly transferred as additional information or data to the first electronic device 137. The same applies to the determination of the time of day and/or duration of a measurement carried out by the measuring apparatus 100. These pieces of information or data may be determined by the time measuring device and likewise concomitantly transferred as additional information or data to the first electronic device 137. Likewise, by means of the scanner device, for example, a code of a batch number of a substance used for the measurement or analysis may be scanned in and forwarded as additional information to the first electronic device 137. Moreover, photographs for example of the locality at which a measurement was carried out by the measuring apparatus 100 may be recorded by the camera device and communicated to the first electronic device 137.

The first electronic device 137, e.g. a central server, may store all these pieces of information and optionally additionally manage or evaluate them. By way of example, on the basis of the scanned-in code of the batch number, the electronic device 137 may determine whether the shelf life was complied with, the correct substance was used for carrying out the measurement, what measurement was carried out, e.g. a pH measurement, etc. On the basis of the data of the time measuring device it is possible to determine whether for example the measurement duration for the measurement by the measuring apparatus was complied with, etc. On the basis of the GPS data, it is furthermore possible to determine whether measurement was carried out at the correct location, etc.

As a result, measurements can be reliably monitored and supervised and furthermore considerably simplified. By way of example, by means of the GPS function, the position data for the measurement can automatically be determined exactly. Furthermore, for example, information or data can also be communicated by the first electronic device 137 to the second or subordinate electronic device 37 and be received by the receiver device of the second electronic device 37 in the case of a wireless interface, e.g. a Bluetooth or radio connection. By way of example, the first or superordinate electronic device 137 can notify the second or subordinate electronic device 37 if there is an error in the measurement because e.g. the shelf life of the substance used for measurement was exceeded, the incorrect substance was used for the measurement, the measurement time was not complied with and/or measurement was carried out at the incorrect location. Likewise, the first or superordinate electronic device 137 can also instruct the second or subordinate electronic devices as to what measurement or measurements should be carried out.

Although the present invention was described above on the basis of the preferred exemplary embodiments, it is not restricted thereto, but rather can be modified in diverse ways. In particular, the above-described embodiments and exemplary embodiments in FIGS. 1-9 can be combined with one another, in particular individual features thereof.

In particular, the invention provides a spectrometer for analyzing a fluid sample and in particular measuring the concentration of at least one analyte in a fluid sample, wherein the spectrometer comprises a measuring apparatus comprising: a sample receptacle device having a sample receptacle for receiving a fluid sample, a light source device for generating a light beam, a light receiver for receiving the light beam and converting the light beam into electrical signals, a measurement path in the beam path of the light beam, into which the fluid sample is introducible, wherein the spectrometer furthermore comprises at least one connection device for connecting an external electronic device to the spectrometer, for evaluating the signals of the light receiver of the measuring apparatus and displaying a result of the evaluation.

In the present description, the term light encompasses light visible to human beings and also light outside the range visible to human beings, depending on the function and purpose of use of the light source device or illumination device and also the type of luminescent sample.

LIST OF REFERENCE SIGNS

1 Spectrometer
2 Sample receptacle device
3 Fluid sample
4 Light source device or illumination device
5 Light beam
6 Photosensor
7 Measurement path
8 Optical waveguide
9 Sample receptacle
11 Energy source
13 Sensor receptacle
14 First section (optical waveguide)
15 Second section (optical waveguide)
20 Analog/digital converter
21 Optical beam path
22 Optical device
23 Sealing device
24 Sample container
25 Opening (sample receptacle device)
26 Opening (sample receptacle device)
27 Elastic section
28 Collar
29 Depression
30 Cover
31 Housing
32 LED
33 LED array
34 Microcontroller
35 Lens
36 Connection device
37 Electronic device
38 Switch device
39 Longitudinal axis
41 First section (sleeve)
42 Receptacle space
43 Second section (sleeve)
44 Third section (sleeve)
45a End side (optical waveguide)
45b Front end
46 Other end side (optical waveguide)
47 Means
49 Housing
50 Sample receptacle space
51 Sample container
52 Sample
53 Cover
54 Housing opening
55 Illumination device
56 Radiation receiver device
57 Cover
58 Closure flap
100 Measuring apparatus
101 GPS device
102 Time measuring device
103 Camera device
104 Storage device
105 Transmitting device
106 Receiver device
107 Scanner device
108 Microphone device
109 Evaluation device
110 Display device
111 Storage device
112 Sleeve
113 Elongate holes
114 End piece
115 Measuring and evaluation apparatus
137 External electronic device

The invention claimed is:

1. A measuring apparatus designed to analyze a fluid sample or a luminescent sample, the measuring apparatus comprising:
   (a) a radiation receiver device for receiving a light beam guided along a measurement path through the fluid sample or radiation emitted by the luminescent sample;
   (b) at least one connection device for connecting an external electronic device for transferring the measurement signals of the radiation receiver device to an evaluation device of the external electronic device for evaluating the measurement signals; and
   (c) a sample receptacle device having a sample receptacle for receiving the fluid sample, wherein the sample receptacle:
      (i) is designed to be equippable with a sample container with the fluid sample; and
      (ii) comprises two openings, one at each opposite side, for leading the sample container through,
      and further wherein each of the two openings tapers in its cross section such that a sample container having a correspondingly tapered cross section can be inserted therein and held in the sample receptacle.

2. The measuring apparatus of claim 1, wherein the connection device is a cable connection, in particular a USB cable connection, or a wireless connection, in particular a Bluetooth or radio connection.

3. The measuring apparatus of claim 1, wherein the measuring apparatus comprises a housing having a sample receptacle space for receiving a sample container, and a sample container for receiving the luminescent sample.

4. The measuring apparatus of claim 1, wherein the measuring apparatus comprises at least one illumination device for illuminating the luminescent sample, wherein the luminescent sample is a photoluminescent sample.

5. The measuring apparatus of claim 1, wherein a plurality of illumination devices are provided, wherein at least two or all illumination devices emit light of the same wavelength or light of different wavelengths for illuminating the luminescent sample.

6. The measuring apparatus of claim 1, wherein the measuring apparatus comprises an illumination device for generating the light beam.

7. The measuring apparatus of claim 6, wherein the illumination device comprises at least one LED (32), in particular laser LED, or an LED array, wherein the LEDs of the LED array are drivable individually or jointly.

8. The measuring apparatus of claim 1, wherein the measurement path is formed in the beam path of the light beam into which the fluid sample is introducible.

9. The measuring apparatus of claim 1, wherein the sample receptacle device is provided fixedly in a housing of the measuring apparatus for the purpose of providing a constant measurement path or is provided such that it is retractable into and extendible from the housing for the purpose of providing a variable measurement path, wherein the measurement path is enlarged by the sample receptacle device being extended from the housing and is shortened by the sample receptacle device being retracted into the housing.

10. The measuring apparatus of claim 9, wherein an optical waveguide is arranged in the sample receptacle device, wherein the sample receptacle device is retractable into and extendible from the housing along the optical waveguide.

11. The measuring apparatus of claim 4, wherein the measuring apparatus comprises a microcontroller for controlling the illumination device by open-loop and/or closed-loop control, wherein the microcontroller is controllable by open-loop and/or closed-loop control in particular by the external electronic device, wherein preferably the illumination duration, the illuminance and/or the illumination interval of the illumination device is controllable by open-loop and/or closed-loop control via the microcontroller.

12. The measuring apparatus of claim 11, wherein the microcontroller is controllable by open-loop and/or closed-loop control by the external electronic device.

13. The measuring apparatus of claim 1, wherein the measuring apparatus comprises an analog/digital converter which converts analog signals of the radiation receiver device into digital signals and transfers them to the microcontroller and/or to an external electronic device connected to the connection device.

14. The measuring apparatus of claim 1, wherein the measuring apparatus comprises a dedicated energy source and/or is connectable to an external energy source by means of the connection device.

15. The measuring apparatus of claim 1, wherein the measuring apparatus comprises a switch device for switching the measuring apparatus on and off.

16. The measuring apparatus of claim 1, wherein the measuring apparatus comprises a storage device.

17. The measuring apparatus of claim 1, wherein the measuring apparatus comprises at least one optical device, in particular at least one lens, one mirror or one prism.

18. The measuring apparatus of claim 1, wherein the sample receptacle has a depression for receiving a sample container, and the sample receptacle and/or the sample container are/is preferably closeable, in particular tightly closeable.

19. The measuring apparatus of claim 1, wherein at least one opening of the sample receptacle has a sealing device for sealing the sample receptacle relative to a sample container received in the sample receptacle.

20. A measuring and evaluation apparatus comprising a measuring apparatus of claim 1 and an electronic device connected to the measuring apparatus.

21. The measuring and evaluation apparatus of claim 20, wherein the electronic device comprises an evaluation device for evaluating the measurement signals of the measuring apparatus.

22. The measuring and evaluation apparatus of claim 20, wherein the electronic device comprises a display device, a GPS device, a time measuring device, a camera device, a storage device, a transmitting device, a receiver device, a scanner device and/or a microphone device.

23. The measuring and evaluation apparatus of claim 20, wherein the electronic device links and/or evaluates the measurement signals with information of the GPS device, the time measuring device, the camera device, the storage device, the scanner device, and/or the microphone device.

24. The measuring and evaluation apparatus of claim 20, wherein the electronic device is a smartphone, a PC, a tablet PC, a server or a laptop.

25. A measurement data system comprising at least one measuring and evaluation apparatus of claim 20 and a second electronic device.

26. The measurement data system of claim 25, wherein the second electronic device is connectable to the respective electronic device of the measuring and evaluation apparatus wirelessly and/or in a wired fashion.

27. The measurement data system of claim 25, wherein the second electronic device is a server, a PC, a smartphone, a smart watch, a laptop or a tablet PC.

\* \* \* \* \*